(12) United States Patent
Von Berg et al.

(10) Patent No.: US 9,918,691 B2
(45) Date of Patent: Mar. 20, 2018

(54) DEVICE AND METHOD FOR DETERMINING IMAGE QUALITY OF A RADIOGRAM IMAGE

(71) Applicant: KONINKLIJKE PHILIPS N.V., Eindhoven (NL)

(72) Inventors: Jens Von Berg, Hamburg (DE); Stewart Young, Hamburg (DE); Heike Carolus, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/503,150

(22) PCT Filed: Oct. 16, 2015

(86) PCT No.: PCT/EP2015/073953
§ 371 (c)(1),
(2) Date: Feb. 10, 2017

(87) PCT Pub. No.: WO2016/066444
PCT Pub. Date: May 6, 2016

(65) Prior Publication Data
US 2017/0224302 A1    Aug. 10, 2017

(30) Foreign Application Priority Data
Oct. 30, 2014   (EP) ..................... 14190995

(51) Int. Cl.
*G06K 9/00* (2006.01)
*A61B 6/00* (2006.01)
(Continued)

(52) U.S. Cl.
CPC ............ *A61B 6/5217* (2013.01); *A61B 6/466* (2013.01); *G06T 7/0014* (2013.01); *G06T 7/62* (2017.01);
(Continued)

(58) Field of Classification Search
CPC . G06T 7/11; G06T 7/66; G06T 7/0014; G06T 2207/30008; G06T 2207/30061; A61B 6/544; A61B 6/466
(Continued)

(56) References Cited

U.S. PATENT DOCUMENTS 5,251,207 A    10/1993   Abensour
6,516,046 B1   2/2003    Frohlich
(Continued)

FOREIGN PATENT DOCUMENTS

JP    01101283 A    4/1992
JP    H1127543 A    1/1999
(Continued)

OTHER PUBLICATIONS

Von Berg, Jens et al "Temporal subtraction of chest radiographs compensating pose differences", Medical Imaging 2011. Proc. of SPIE vol. 7962.
(Continued)

*Primary Examiner* — Daniel Mariam (57) ABSTRACT

A device (1) for determining image quality of a radiogram image includes: an acquiring module (10), which is configured to acquire the radiogram image; a segmentation module (20), which is configured to segment a thoracic bone structure on the acquired radiogram image into segmented thoracic bone structure contours and a tissue structure on the acquired radiogram image into segmented tissue structure contours; and a quality-determination module (30), which is configured to determine a image quality coefficient for the acquired radiogram image based on a comparison of a first position of the segmented thoracic bone structure contours with a second position of the segmented tissue structure contours.

18 Claims, 4 Drawing Sheets

(51) Int. Cl.
  *G06T 7/00* (2017.01)
  *G06T 7/62* (2017.01)
(52) U.S. Cl.
  CPC ..... *A61B 6/544* (2013.01); *G06T 2207/10124* (2013.01); *G06T 2207/30061* (2013.01)
(58) Field of Classification Search
  USPC .................................................. 382/128, 132
  See application file for complete search history.

(56) References Cited

U.S. PATENT DOCUMENTS

| 8,571,290 | B2* | 10/2013 | Wang ........................ G06T 5/00 382/131 |
| 2003/0081734 | A1 | 5/2003 | Nicolas |
| 2005/0238138 | A1 | 10/2005 | Imai |
| 2006/0039529 | A1 | 2/2006 | Tsubaki |
| 2008/0260226 | A1 | 10/2008 | Moriya |
| 2009/0296883 | A1 | 12/2009 | Saito |
| 2014/0185740 | A1 | 7/2014 | Chen |

FOREIGN PATENT DOCUMENTS

| JP | 2010220902 A | 10/2010 |
| WO | 199942031 A1 | 8/1999 |

OTHER PUBLICATIONS

Gavrielides, Marios A. et al "Automated alignment of serial thoracic scans using bone structure descriptors", Medical Imaging 2007, Proc. of SPIE vol. 6514.

Ahmad, Naveed "Tips and Techniques for Decubitus and Oblique Chest X-Rays", X-Ray Patient Positioning Manual, 2001.

Dworzak, J. et al, "3D reconstruction of the human rib cage from 2d projection images using a statistical shape model" International journal of computer assisted radiology and surgery, vol. 5, No. 2, pp. 111-124, 2010.

Gooβen, A. et al "Quantitative Image Quality in Digital Radiographs", Philips Technical Report PR-TN 2011/00386. 2011.

* cited by examiner

DEVICE AND METHOD FOR DETERMINING IMAGE QUALITY OF A RADIOGRAM IMAGE

CROSS-REFERENCE TO PRIOR APPLICATIONS

This application is the U.S. National Phase application under 35 U.S.C. § 371 of International Application No. PCT/EP2015/073953, filed on Oct. 16, 2015, which claims the benefit of European Patent Application No. 14190995.2, filed on Oct. 30, 2014. These applications are hereby incorporated by reference herein.

FIELD OF THE INVENTION

The present invention relates to the field of image quality analysis, determination, and assessment. Particularly, the present invention relates to a device and a method for determining image quality of a radiogram image.

BACKGROUND OF THE INVENTION

U.S. Pat. No. 6,516,046 B1 describes a method for exact positioning of a patient for radiotherapy or radiosurgery comprising the steps of pre-positioning the patient relative to a linear accelerator, producing at least one X-ray image of the patient or one of body parts in the vicinity of the radiation treatment target, mapping the X-ray image and detecting a positional error on the basis of specific landmarks in the image.

U.S. 2003/0081734 A1 describes a low-dose exposure aided positioning system for digital radiography, a system and a method for improved imaging of a patient through the use of low-dose exposure aided positioning is provided, the patient is positioned in the X-ray system and then imaged with a low-dose pre-shot to verify the positioning of the patient. If the patient's positioning is acceptable, the patient is then imaged with a full-dose X-ray exposure.

US 2014/0185740 A1 describes an automatic scanning and positioning apparatus for a scout image, the apparatus comprising a receiving means, for receiving a scout image of a subject obtained through scouting scanning; a checking and determining means, for automatically checking at least one position in the scout image according to a plurality of information contained in the scout image, and automatically determining a scanning scope based on the at least one position.

In many fields of digital X-ray radiography bad quality of images is induced by improper or inappropriate patient positioning that has a deep impact on the quality of recorded images.

Positioning errors are one of the most frequently done observed errors in X-ray acquisition. Positioning errors may degrade the diagnostic value of a radiograph, e.g. a lung tissue abnormality is overlaid with the scapula due to malpositioning errors, and in consequence the abnormality is overlooked. Positioning errors may also preclude the desired diagnosis, e.g. the target organ is not completely visible (e.g. missing lung, missing lung apex), or acquired from an imperfect angle (e.g. for an orthopaedic question).

In such cases the X-ray acquisition has to be repeated. Strong variability in acquisition not well adhering consistently to pre-defined standards was also stated as the main problem in image acquisition in the area of tuberculosis in our investigations. Thus, following adherence to positioning standards is an important factor for the value of X-ray images.

SUMMARY OF THE INVENTION

There may be a need to improve systems and methods for image quality analysis.

An aspect of the present invention relates to a device for determining image quality of a radiogram image, the device comprising an acquiring module, which is configured to acquire the radiogram image; and a segmentation module, which is configured to segment a thoracic bone structure on the acquired radiogram image into segmented thoracic bone structure contours and a tissue structure on the acquired radiogram image into segmented tissue structure contours; and a quality-determination module, which is configured to determine an image quality coefficient for the acquired radiogram image based on a comparison of a first position of the segmented thoracic bone structure contours with a second position of the segmented tissue structure contours.

In other words, the present invention relates to diagnostic X-ray radiography or to chest radiography. When acquiring chest radiographs, patient positioning errors are a common course of inadequate image quality. Positioning errors may degrade the diagnostic value of a radiograph.

The term "image quality" as used by the present invention may refer to a characteristic of an image that measures the perceived image degradation (typically, compared to an ideal or perfect image). Imaging systems may introduce some amounts of distortion or artifacts in the signal, so the quality assessment is an important problem.

The present invention advantageously proposes to automatically determine the quality of a patient positioning from a recorded radiograph image. For instance, the thoracic bones and two lung fields as visible on the image are segmented. By using geometric properties of the segmented thoracic bones, image quality measures can be provided.

An automatic segmentation algorithm may be provided that segments the lung fields, clavicles and ribs. Further, also a segmentation of the scapulae may be provided. Once the bones are segmented, automatic measures can be performed. For example, it may be tested whether the scapulae contours intersect with the lung field contour, indicating inappropriate positioning of the scapulae. Further, for example, the apex-to-clavicle distance is measured, being a direct quality indicator.

Further, the present invention advantageously may provide that a patient rotation with respect, for instance, to an optical axis of the image recording apparatus can be determined using a three-dimensional thoracic model based on the segmented rib structures.

The present invention advantageously allows a proper patient positioning. The present invention proposes an automatic method to determine a patient position. The method derives a positioning quality measure from the automatic segmentation of the thoracic bones and the lung field. This measures supports quality assurance for patient positioning.

The present invention advantageously allows an improved patient positioning in acquiring chest X-ray images.

According to the present invention, positioning errors may also include that a target organ is not completely visible due to a wrong position or an acquiring of the image from an imperfect angle, for instance out of a predefined and suitable angle range. This advantageously allows minimizing the positioning errors.

The present invention advantageously allows that images are acquired within a wide in other words still sufficient and acceptable for image quality range of patient positions. The present invention advantageously proposes to automatically determine the measures of positioning quality from a radiograph by using geometric properties of the thoracic bones in the image. Further, the present invention provides image quality measures, wherein the bones are segmented in the image.

According to a further, second aspect of the present invention, a method is provided, the method being a method for determining image quality of a radiogram image, the method comprising the steps of: acquiring the radiogram image by means of an acquiring module; segmenting a thoracic bone structure on the acquired radiogram image into segmented thoracic bone structure contours and a tissue structure on the acquired radiogram image into segmented tissue structure contours by means of a segmentation module; and determining an image quality coefficient for the acquired radiogram image based on a comparison of a first position of the segmented thoracic bone structure contours with a second position of the segmented tissue structure contours by means of a quality-determination module.

According to an exemplary embodiment of the present invention, the quality-determination module is configured to determine the image quality coefficient based on a deviation of the first position with respect to a set of predefined first position ranges. In other words it may be determined whether the first position is within the range defined by the set of predefined first position ranges. This advantageously allows avoiding losses of image quality due to positioning errors.

According to an exemplary embodiment of the present invention, the quality-determination module is configured to determine the image quality coefficient based on a deviation of the second position with respect to a set of predefined second position ranges. In other words it may be determined whether the second position is within the range defined by the set of predefined second position ranges. This advantageously allows avoiding losses of image quality due to positioning errors.

According to an exemplary embodiment of the present invention, the quality-determination module is configured to determine an intersection coefficient characterizing a level of intersections of the segmented thoracic bone structure contours with the segmented tissue structure contours. This advantageously allows providing a high image quality or contrast even if intersecting structures are present or near the region of interest.

The term "intersection coefficient" as used by the present invention may refer to a characteristic of an image if at least two imaged structures showing partial transparency or translucency and these structures at least partially are imaged to the same image area, the resulting imaged picture information may comprise structural information from both structures, wherein the intersection coefficient describes the level of overlapping.

According to an exemplary embodiment of the present invention, the quality-determination module is configured to determine the image quality coefficient based on the intersection coefficient. This advantageously allows providing a high image quality.

According to an exemplary embodiment of the present invention, the quality-determination module is configured to determine a position of a patient during an acquisition of the radiogram image with respect to an optical axis of an X-ray camera. This advantageously allows reducing an applied dose of X-ray during image recording.

According to an exemplary embodiment of the present invention, the quality-determination module is configured to determine the image quality coefficient based on the determined position of the patient during the acquisition of the radiogram image. This advantageously allows reducing the applied dose to the patient.

According to an exemplary embodiment of the present invention, the segmentation module is configured to segment a lung field structure into segmented lung field structure contours or a scapulae structure into segmented scapulae structure contours or a clavicle structure into segmented clavicle structure contours or a rib structure into segmented rib structure contours as the segmentation of the tissue structure. This advantageously allows using image analysis techniques for an automatic segmentation of anatomical structures.

According to an exemplary embodiment of the present invention, the quality-determination module is configured to determine the image quality coefficient for the acquired radiogram image based on a comparison of the first position of the segmented thoracic bone structure contours with a second position of the segmented lung field structure contours or the segmented scapulae structure contours or the segmented clavicle structure contours or the segmented rib structure contours.

According to an exemplary embodiment of the present invention, the quality-determination module is configured to determine the image quality coefficient based on a measured apex-to-clavicle distance.

A computer program performing the method of the present invention may be stored on a computer-readable medium. A computer-readable medium may be a floppy disk, a hard disk, a CD, a DVD, an USB (Universal Serial Bus) storage device, a RAM (Random Access Memory), a ROM (Read Only Memory) and an EPROM (Erasable Programmable Read Only Memory). A computer-readable medium may also be a data communication network, for example the Internet, which allows downloading a program code.

The methods, systems and devices described herein may be implemented as software in a Digital Signal Processor, DSP, in a micro-controller or in any other side-processor or as hardware circuit within an application specific integrated circuit, ASIC, CPLD or FPGA.

The present invention can be implemented in digital electronic circuitry, or in computer hardware, firmware, software, or in combinations thereof, e.g. in available hardware of a medical device or in new hardware of a medical device dedicated for processing the methods described herein.

A more complete appreciation of the invention will be more clearly understood by reference to the following schematic drawings, which are not to scale, wherein.

DETAILED DESCRIPTION OF EMBODIMENTS

The illustration in the drawings is purely schematic and does not intend to provide scaling relations or size information. In different drawings or figures, similar or identical elements are provided with the same reference numerals. Generally, identical parts, units, entities or steps are provided with the same reference symbols in the description.

Figure 1:
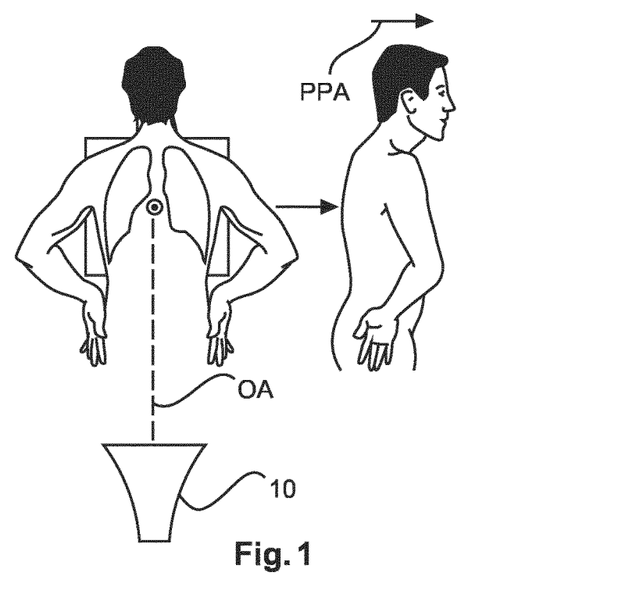
FIG. 1 shows a schematic diagram of a position required for an optimal patient's position for a chest radiograph image acquired from posterior to anterior for explaining the present invention.

FIG. 1 shows a position required for an optimal patient's position for a chest PA radiograph, PA: radiation from posterior to anterior. The relative position of a patient to an optical axis OA of an X-ray camera of an acquiring module 10 is shown in FIG. 1.

In other words, the acquiring module 10 may comprise an X-ray camera or an X-ray detector or any other optical instrument that records images per radiography that can be stored directly.

The positioning of the patient may be defined by a position vector PPA describing the position of the patient with respect to a reference system or as a relative position with respect to the optical axis OA of an X-ray camera. The positioning of the patient may have influence on the quality of the recorded radiogram image, e.g. due to male-positioning various tissue structures may overlap or cover each other.

Figure 2:
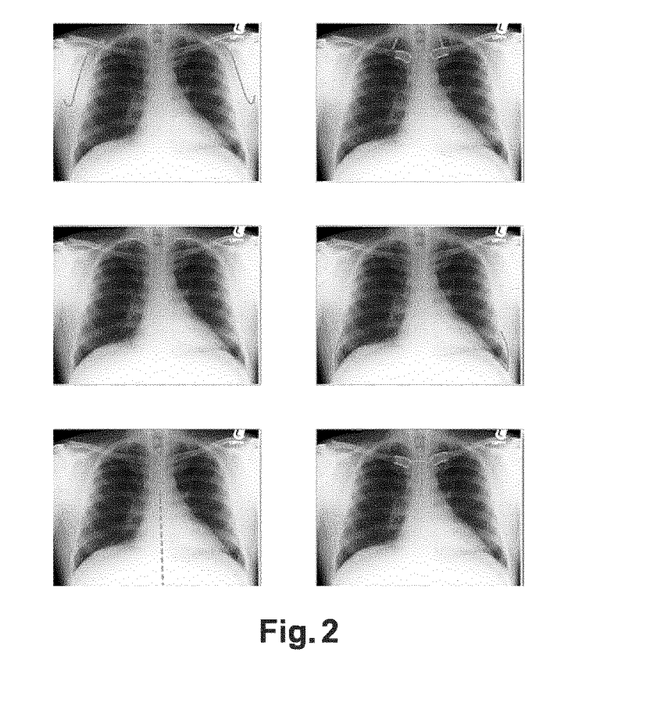
FIG. 2 a schematic diagram of a plurality of acquired radiogram images for explaining the present invention.

FIG. 2 shows a schematic diagram of a plurality of acquired radiogram images for explaining the present invention, criteria determining a proper patient positioning for chest PA radiography are defined. On the top left radiogram image, a scapula of the lung field is shown, on the middle left radiogram image, lung apices on the X-ray are shown, on the lower left image, a radiogram is shown, wherein spine and trachea are centered.

The radiogram image on the upper right of FIG. 2 shows lung apices which are 5 cm above the clavicles. The middle right radiogram image of FIG. 2 shows costophrenic angles on the X-ray. The radiogram on the lower right of FIG. 2 shows clavicles equidistance to vertebral column.

Figure 3:
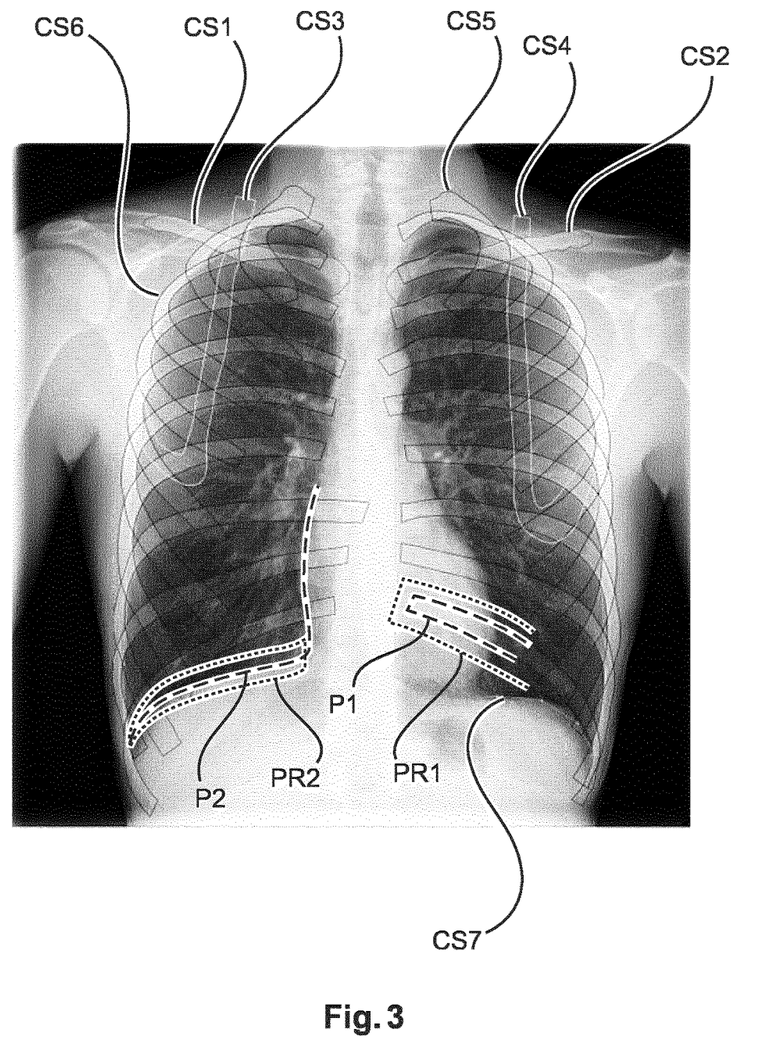
FIG. 3 a schematic diagram of a segmentation of both lung fields, the clavicles, the scapulae inside the lung field and the ribs in the lung field for explaining the present invention.

FIG. 3 shows a number of reference structures, which reflect the position of the patient and which may be determined automatically from the image.

For instance, according to an exemplary embodiment of the present invention, the thoracic bones and two lung fields are used for this purpose. An automatic segmentation algorithm may be used to obtain the contours of the structures. The lung fields may be segmented. Further, the clavicles and the ribs are segmented.

A first pair of tissue structure CS1, CS2 may be represented by left and right clavicles, a second pair of tissue structures CS3, CS4 may be given by the left and right scapulae inside the lung field. The ribs in the lung field are represented by the tissue structures CS5, CS6, the two lung fields by CS7.

According to an exemplary embodiment of the present invention, once, the bones are delineated, further measurements are performed automatically, for instance, it is tested whether the scapulae contours intersect with the lung field contours, indicating inappropriate positioning of the scapulae. The level of intersections occurring with these different tissue structures may be determined and an intersection coefficient describing the occurring level of intersections may be calculated.

According to an exemplary embodiment of the present invention, an intersection of the lung field contour with the image boundaries may also be tested, which would indicate a missing apex or missing costophrenic angle, characterizing an intersection at the bottom of the image. The apex of the lung (Latin: apex pulmonis) is the rounded upper part of the human lung. It extends into the root of the neck, reaching between 2.5 centimeters (0.98 in) and 4 centimeters (1.6 in) above the level of the sternal end of the first rib.

According to an exemplary embodiment of the present invention, the apex to clavicle distance may be measured as well being a direct quality indicator. Further, according to an exemplary embodiment of the present invention, a respiratory state may be checked by analysis of the diaphragm contour representing a part of the lung field contour.

According to an exemplary embodiment of the present invention, local indicators like the media borders of the clavicles may be explicit and easy to analyze. The present invention may be advantageously applied in various applications: It can provide direct feedback to the operator performing an acquisition. This could be useful to enable decisions regarding the required retake of an image and to enable the operator to learn to optimize the patient positioning. A scheme indicating actual and desired bone positions overlaid with the radiograph is a further application for the present invention.

Further, according to an exemplary embodiment of the present invention, the system may be used to collect and aggregate in X-ray machines, X-ray imaging systems or other medical imaging system. Further, the medical imaging system may record a pre-shot image. This may provide the opportunity to reduce radiation exposure to the patient in the case when the quality measure is sub-optimal.

According to an exemplary embodiment of the present invention, the quality determination module 30 may be configured to determine an image quality coefficient for the acquired radiogram image based on a comparison of a first position P1 of the segmented thoracic bone structure contours with a second position P2 of the segmented tissue structure contours.

Further, according to an exemplary embodiment of the present invention, regarding the first position P1 of the segmented thoracic bone structure contours on the radiogram image a range or an area on the radiogram image permissible for the first position P1 may be determined by the quality determination module 30 or predefined, resulting in a set of predefined first position ranges PR1.

The same applies to the second position P2 of the segmented tissue structure contours, the second position P2 may be restricted to be located within a second position range PR2 in order that a sufficient image quality is reached, since only for the case of sufficiently accurate patient positioning, which is determined by analyzing tissue structure positions.

According to an exemplary embodiment of the present invention, further ranges for the second position P2 may be used for defining different quality factors of the radiogram image. The quality-determination module 30 may be configured to determine the image quality coefficient based on a deviation of the second position P2 with respect to a set of predefined second position ranges PR2.

In other words it may be determined whether the second position is within the range defined by the set of predefined second position ranges.

Figure 4:
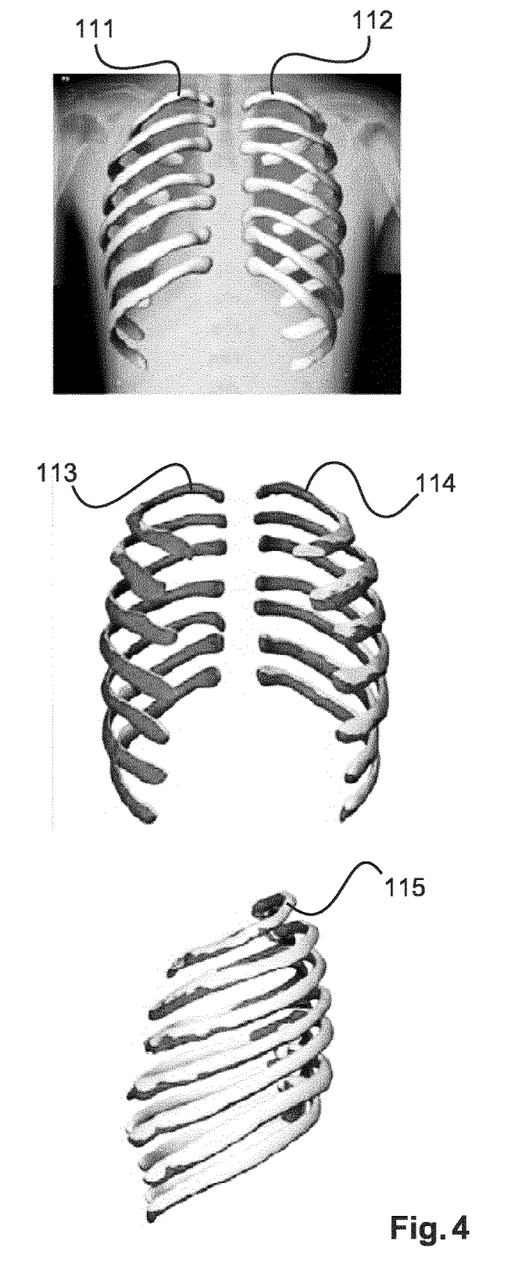
FIG. 4 shows a schematic diagram of an estimating of a patient pose by use of a three-dimensional ribcage model for explaining the present invention.

FIG. 4 shows a schematic diagram of an estimating of a patient pose by use of a three-dimensional rib cage model for explaining the present invention. FIG. 4 shows multiple three-dimensional ribcage models 111, 112, 113, 114, 115 for explaining the present invention.

The three-dimensional rib cage model may be used as a reconstruction method that is based on a three-dimensional statistical shape model, SSM, of the rib cage, which is adapted to the recorded two-dimensional projection images of an individual rib cage. The processing of extracting the structure and modelling the structure in three-dimensional space is shown in FIG. 4.

Figure 5:
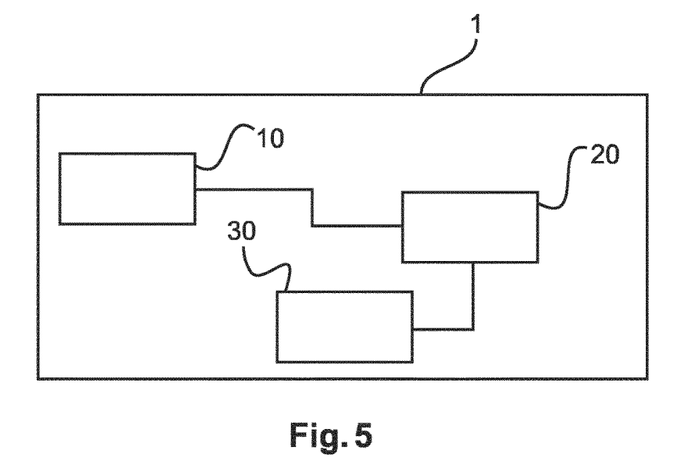
FIG. 5 shows a schematic diagram of a device for determining image quality of a radiogram image according to an exemplary embodiment of the present invention.

According to an exemplary embodiment of the present invention, from the estimated three-dimensional transformation it is possible to derive a quality measure more robustly than based on a single local indicator. A rotation angle around the spinal axis, deviation from an ideal or standard position may be a further basis for such a measure. FIG. 5 shows a device for determining image quality of a radiogram image according to an exemplary embodiment of the present invention.

A device 1 may comprise an acquiring module 10, a segmentation module 20, and a quality determination module 30.

The acquiring module 10 may be configured to acquire a radiogram image, the radiogram image may be an image recorded by a radiographic imaging system using any kind of medical imaging technique that uses tissue penetrating electromagnetic radiation other than visible light, especially X-rays.

The segmentation module 20 may be configured to segment a thoracic bone structure on the acquired radiogram image into segmented thoracic bone structure contours and may be further configured to segment a tissue structure on the acquired radiogram image into segmented tissue structure contours.

The quality determination module 30 may be configured to determine an image quality coefficient for the acquired radiogram image based on a comparison of a first position P1 of the segmented thoracic bone structure contours with a second position P2 of the segmented tissue structure contours.

The image quality coefficient may be used to determine if the quality of a recorded image is sufficient for a certain purpose, this may be accomplished by defining different ranges for the image quality coefficient, wherein a comparison of an actual or specific image quality coefficient value with the ranges may indicate whether a certain quality level is reached by the image.

Figure 6:
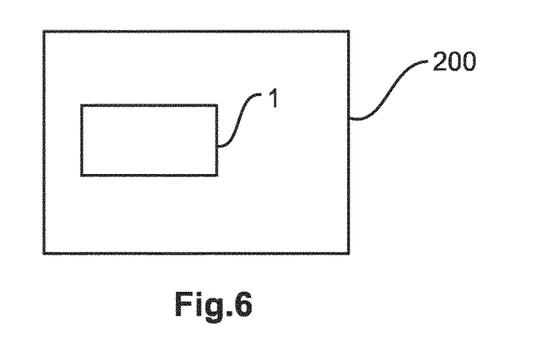
FIG. 6 shows a schematic diagram of a medical device according to an exemplary embodiment of the present invention.

FIG. 6 shows a schematic diagram of a medical device according to a further exemplary embodiment of the present invention.

A medical imaging device 200 may comprise the device for determining the quality of a radiogram image. The medical imaging device 200 may be a radiographic imaging system using any kind of imaging technique that uses electromagnetic radiation other than visible light, especially X-rays, to view the internal structure of a non-uniformly composed and opaque object (i.e. a non-transparent object of varying density and composition) such as the human body.

Figure 7:
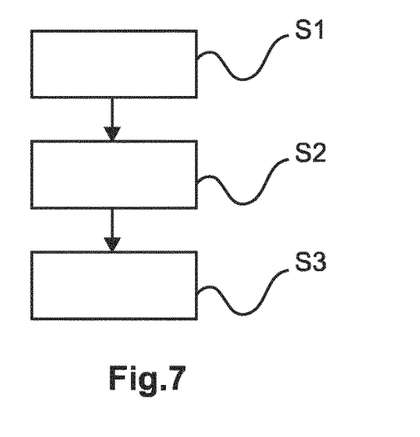
FIG. 7 shows a schematic flowchart diagram of a method for determining image quality of a radiogram image according to an exemplary embodiment of the present invention.

FIG. 7 shows a schematic diagram of a method for determining image quality of a radiogram image according to a further exemplary embodiment of the present invention.

The method as depicted in FIG. 7 may comprise the following steps:

as a first step of the method, acquiring S1 the radiogram image by means of an acquiring module 10 may be performed.

as a second step of the method, segmenting S2 a thoracic bone structure on the acquired radiogram image into segmented thoracic bone structure contours and the tissue structure on the acquired radiogram image into segmented tissue structure contours by means of a segmentation module may be performed.

as a third step of the method, determining an image quality coefficient for the acquired radiogram image based on a comparison of a first position of the segmented thoracic bone structure contours with a second position of the segmented tissue structure contours by means of a quality determination module 30 may be performed.

It has to be noted that embodiments of the present invention are described with reference to different subject-matters. In particular, some embodiments are described with reference to method type claims, whereas other embodiments are described with reference to the device type claims.

However, a person skilled in the art will gather from the above and the foregoing description that, unless otherwise notified, in addition to any combination of features belonging to one type of the subject-matter also any combination between features relating to different subject-matters is considered to be disclosed within this application.

However, all features can be combined providing synergetic effects that are more than the simple summation of these features.

While the present invention has been illustrated and described in detail in the drawings and the foregoing description, such illustration and description are to be considered illustrative or exemplary and not restrictive; the present invention is not limited to the disclosed embodiments.

Other variations to the disclosed embodiments can be understood and effected by those skilled in the art and practicing the claimed invention, from a study of the drawings, the disclosure, and the appended claims.

In the claims, the word "comprising" does not exclude other elements or steps, and the indefinite article "a" or "an" does not exclude a plurality. Any reference signs in the claims should not be construed as limiting the scope.

The invention claimed is:

1. A device for determining image quality of a radiogram image, the device comprising:
    an acquiring module, which is configured to acquire the radiogram image;
    a segmentation module, which is configured to segment a thoracic bone structure on the acquired radiogram image into segmented thoracic bone structure contours and a tissue structure on the acquired radiogram image into segmented tissue structure contours; and
    a quality-determination module, which is configured to determine a image quality coefficient for the acquired radiogram image based on a comparison of a first position of the segmented thoracic bone structure contours with a second position of the segmented tissue structure contours.

2. The device according to claim 1,
    wherein the quality-determination module is configured to determine the image quality coefficient based on a deviation of the first position with respect to a set of predefined first position ranges.

3. The device according to claim 1,
wherein the quality-determination module is configured to determine the image quality coefficient based on a deviation of the second position with respect to a set of predefined second position ranges.

4. The device according to claim 1,
wherein the quality-determination module is configured to determine an intersection coefficient characterizing a level of intersections of the segmented thoracic bone structure contours with the segmented tissue structure contours.

5. The device according to claim 4,
wherein the quality-determination module is configured to determine the image quality coefficient based on the intersection coefficient.

6. The device according to claim 1,
wherein the quality-determination module is configured to determine a position of a patient during an acquisition of the radiogram image with respect to an optical axis of an X-ray camera.

7. The device according to claim 6,
wherein the quality-determination module is configured to determine the image quality coefficient based on the determined position of the patient during the acquisition of the radiogram image.

8. The device according to claim 1,
wherein the segmentation module is configured to further segment a lung field structure into segmented lung field structure contours or a scapulae structure into segmented scapulae structure contours or a clavicle structure intro segmented clavicle structure contours or a rib structure into segmented rib structure contours as the segmentation of the tissue structure.

9. The device according to claim 8,
wherein the quality-determination module is configured to determine the image quality coefficient for the acquired radiogram image based on a comparison of the first position of the segmented thoracic bone structure contours with a second position of the segmented lung field structure contours or the segmented scapulae structure contours or the segmented clavicle structure contours or the segmented rib structure contours.

10. The device according to claim 1,
wherein the quality-determination module is configured to determine the image quality coefficient based on a measured apex-to-clavicle distance.

11. A medical imaging system comprising a device according to claim 10.

12. A method for determining image quality of a radiogram image, the method comprising the steps of:
acquiring the radiogram image by means of an acquiring module;
segmenting a thoracic bone structure on the acquired radiogram image into segmented thoracic bone structure contours and a tissue structure on the acquired radiogram image into segmented tissue structure contours by means of a segmentation module; and
determining an image quality coefficient for the acquired radiogram image based on a comparison of a first position of the segmented thoracic bone structure contours with a second position of the segmented tissue structure contours by means of a quality-determination module.

13. The method according to claim 12,
wherein the step of determining the image quality coefficient is performed based on a deviation of the first position with respect to a set of predefined first position ranges.

14. The method according to claim 12,
wherein the step of determining the image quality coefficient is performed based on a deviation of the second position with respect to a set of predefined second position ranges.

15. A non-transitory computer-readable medium storing a program code for controlling a computer to perform the method according to claim 12.

16. A device for determining image quality of a radiogram image, the device comprising:
one or more computer processors configured to:
acquire the radiogram image,
segment a thoracic bone structure on the acquired radiogram image into segmented thoracic bone structure contours and a tissue structure on the acquired radiogram image into segmented tissue structure contours, and
determine an image quality coefficient for the acquired radiogram image based on a comparison of a first position of the segmented thoracic bone structure contours with a second position of the segmented tissue structure contours.

17. The device according to claim 16, further including:
a display device configured to display a visual indication of the image quality coefficient.

18. The device according to claim 17, wherein the display device is further configured to display the radiogram.

* * * * *